US005626851A

United States Patent [19]

Clark et al.

[11] Patent Number: 5,626,851
[45] Date of Patent: May 6, 1997

[54] ROTAVIRUS REASSORTANT VACCINE

[75] Inventors: H. Fred Clark; Paul Offit, both of Philadelphia, Pa.; Stanley A. Plotkin, Paris, France

[73] Assignees: The Wistar Institute of Anatomy and Biology; The Children's Hospital of Philadelphia, both of Philadelphia, Pa.

[21] Appl. No.: 353,547

[22] Filed: Dec. 9, 1994

Related U.S. Application Data

[63] Continuation-in-part of Ser. No. 121,220, Sep. 14, 1990, abandoned, and Ser. No. 249,696, May 26, 1994, abandoned, which is a continuation of Ser. No. 902,321, Jun. 22, 1992, abandoned, which is a continuation-in-part of Ser. No. 558,884, Jul. 2, 1990, abandoned, which is a continuation-in-part of Ser. No. 126,477, Nov. 30, 1987, abandoned, said Ser. No. 121,220, is a continuation of Ser. No. 558,884, which is a continuation-in-part of Ser. No. 126,477.

[51] Int. Cl.$^6$ .......................... A61K 39/12; A61K 39/295; C12N 7/00; C12Q 1/70
[52] U.S. Cl. ................... 424/205.1; 424/93.1; 424/93.2; 435/5; 435/235.1
[58] Field of Search ....................... 424/93.1, 93.2, 424/205.1; 435/5, 235.1, 172.3

[56] References Cited

U.S. PATENT DOCUMENTS

| | | | |
|---|---|---|---|
| 3,293,129 | 12/1966 | Baker | 167/218.1 |
| 4,190,645 | 2/1980 | Almeida | 424/236 |
| 4,205,131 | 5/1980 | Almeida | 435/235 |
| 4,341,763 | 7/1982 | Zygrarch | 424/215.1 |
| 4,341,870 | 7/1982 | Wyatt et al. | 435/237 |
| 4,571,385 | 2/1986 | Greenberg et al. | 435/172.3 |
| 4,624,850 | 11/1986 | Albert et al. | 424/215.1 |
| 4,636,385 | 1/1987 | Plotkin et al. | 424/215.1 |
| 4,704,275 | 11/1987 | Wyatt et al. | 424/215.1 |
| 4,751,080 | 6/1988 | Wyatt et al. | 424/205.1 |
| 4,853,333 | 8/1989 | Hsiao et al. | 435/254.21 |
| 4,861,864 | 8/1989 | Atkinson et al. | 530/324 |
| 4,927,628 | 5/1990 | Chanock et al. | 424/205.1 |
| 5,053,406 | 10/1991 | Smka et al. | 514/182 |
| 5,298,244 | 3/1994 | Redmond et al. | 424/186.1 |
| 5,332,658 | 7/1994 | Dyall-Smith et al. | 435/5 |

FOREIGN PATENT DOCUMENTS

| | | |
|---|---|---|
| 0130906 | 1/1985 | European Pat. Off. |
| 0152295 | 8/1985 | European Pat. Off. |
| 0192404 | 8/1986 | European Pat. Off. |
| 0235391 | 9/1987 | European Pat. Off. |
| 0323708 | 7/1989 | European Pat. Off. |
| 323708A | 12/1989 | European Pat. Off. |
| 1276218 | 6/1972 | United Kingdom |
| 2009786 | 6/1979 | United Kingdom |
| WO92/01784 | 2/1992 | WIPO |
| WO92/07941 | 5/1992 | WIPO |
| WO92/08786 | 5/1992 | WIPO |
| WO94/01134 | 1/1994 | WIPO |

OTHER PUBLICATIONS

H F. Clark et al, "Rotavirus Isolate WI61 Representing a Presumptive New Human Serotype", J. Clin. Microbiol., 25(9):1757–1762 (Sep., 1987) [Clark I].

H F. Clark et al. "Rotavirus Vaccines", Vaccines, Plotkin S.A., Mortimer E.A., eds. (Phildelphia, W.B. Saunders), pp. 517–525 (1988) [Clark II].

H F. Clark et al, "Approaches to Immune Protection Against Rotavirus Diarrhea of Infants", Immunization Monitor, 3(3):3–15 (Aug., 1989) [Clark III].

H F. Clark et al, "Serotype 1 Reassortant of Bovine Rotavirus WC3, Strain WI79–9, Induces a Polytypic Antibody Response in Infants", Vaccine, 8:327–332 (Aug., 1990) [Clark IV].

H F. Clark et al, "Immune Protection of Infants Against Rotavirus Gastroenteritis by a Serotype 1 Reassortant of Bovine Rotavirus WC3", J. Infect. Dis., 161:1099–1104 (Jun., 1990) [Clark V].

H F. Clark et al, "Immune Response of Infants and Children to Low–Passage Bovine Rotavirus (Strain WC3)", Amer. J. Dis. Child., 140:350–356 (Apr., 1986) [Clark VI].

H F. Clark et al, "Diverse Serologic Response to Rotavirus Infection of Infants in a Single Epidemic", Ped. Infect. Dis., 4(6):626–631 (Nov., 1985) [Clark VII].

H F. Clark et al., "A Presumptive New Serotype of Human Rotavirus", 1986 ASM Annual Meeting, Washington, DC, Abstract, (Mar., 1986) [Clark VIII].

H F. Clark, "Rotavirus Vaccine", Seminars Ped. Infect. Dis., 2(3):202–206 (Jul., 1991) [Clark IX].

H F. Clark et al, "Infant Responses to Bovine Rotavirus WC3 Reassortants Containing Human Rotavirus VP7, VP4, or VP7+VP4", in Abstracts of the ICAAC, Anaheim, CA, p. 343 (1992) [Clark X].

P. Offit et al, "Molecular Basis of Rotavirus Virulence: Role of Gene Segment 4", J. Virol., 57(1):46–49 (Jan., 1986) [Offit I].

P. Offit et al, "Identification of the Two Rotavirus Genes Determining Neutralization Specificities", J. Virol., 57:376–378 (Jan., 1986) [Offit II].

P. Offit et al, "Reassortant Rotaviruses Containing Structural Proteins vp3 and vp7 from Different Parents Induce Antibodies Protective Against each Parental Serotype", J. Virol., 60(2):491–496 (Nov., 1986) [Offit III].

P. Offit et al, "Maternal Antibody–Mediated Protection Against Gastroenteritis due to Rotavirus in Newborn Mice is Dependent on both Serotype and Titer of Antibody", J. Infect. Dis., 152(6):1152–1158 (Dec., 1985) [Offit IV].

(List continued on next page.)

Primary Examiner—George C. Elliott
Assistant Examiner—Thanda Wai
Attorney, Agent, or Firm—Howson and Howson

[57] ABSTRACT

The present invention provides novel rotavirus reassortants, vaccines employing the novel reassortants and methods for their preparation and administration. One such reassortant contains the gene encoding the v.p.7 neutralization antigen of a human rotavirus. Another reassortant contains the gene encoding the v.p.4 neutralization antigen of a human rotavirus. The remaining genes are provided solely from the bovine rotavirus WC3 strain, or from both the human and bovine strains.

39 Claims, No Drawings

OTHER PUBLICATIONS

P. Offit et al, "Outer Capsid Glycoprotein vp7 is Recognized by Cross-Reactive, Rotavirus-Specific, Cytotoxic T Lymphocytes", Virology, 184(2):563–568 (1991) [Offit V].

P. Offit et al, "Rotavirus-Specific Cytotoxic T Lymphocyte Response of Mice after Oral Inoculation with Candidate Rotavirus Vaccine Strains RRV or WC3", J. Infect. Dis., 160(5):783–788 (Nov., 1989) [Offit VI].

K. Midthun et al., "Single Gene Substitution Rotavirus Reassortants Containing the Major Neutralization Protein (VP7) of Human Rotavirus Serotype 4", J. Clin. Microbiol., 24(5):822–826 (Nov., 1986) [Midthun I].

K. Midthun et al., "Reassortant Rotaviruses as Potential Live Rotavirus Vaccine Candidates", J. Virol., 53(3):949–954 (Mar., 1985) [Midthun II].

Y. Hoshino et al, "Independent Segregation of Two Antigenic Specificities (WP3 and VP7) Involved in Neutralization of Rotavirus Infectivity", Proc. Natl. Acad. Sci. USA, 82:8701–8704 (Dec., 1985) [Hoshino I].

Y. Hoshino, "Genetic Studies of Rotavirus Virulence", Summary, Third NIH Rotavirus Workshop, Bethesda, MD, p. 50 (Sep. 1988) [Hoshino II].

R. Daum et al., "New Developments in Vaccines", Advances in Pediatric Infectious Diseases, vol. 6, pp. 1–57 (1991).

J. Walsh et al., "Special Article –Selective Primary Health Care –An Interim Strategy for Disease Control in Developing Countries", New Eng. J. Med., 301(18):967–974 (Nov., 1979).

I. deZoysa et al., "Interventions for the Control of Diarrhoeal Diseases Among Young Children: Rotavirus and Cholera Immunization", Bull. WHO, 63(3):569–583 (1985).

M-S. Ho et al., "Morbidity and Mortality Associated with Rotavirus Diarrhea in the U.S.", 27th Interscience Conf. Antimicrobiol Agents Chemotherapy, Abstract No. 13 (1987).

M. Estes et al., "Antigenic Structure of Rotaviruses", Immunochemistry of Viruses, Elsevier, Amsterdam, pp. 389–405 (1985) [Estes I].

M. Estes et al, "Molecular Biology and Immunology of Rotavirus Infections", Immunol. Invest., 18(1–4):571–581 (1989) [Estes II].

M. Estes, "Rotaviruses and Their Replication", Ch. 48 in Virology, 2d ed., pp. 1329–1352, ed. by Fields, Knipe et al, New York (1990) [Estes III].

R. Wyatt et al., "Definition of Human Rotavirus Serotypes by Plaque Reduction Assay", Infect. and Immun., 37(1):110–115 (Jul., 1982).

S. Matsuno et al, "A Candidate for a New Serotype of Human Rotavirus", J. Virol., 54(2):623–624 (May, 1985) [Matsuni I].

S. Matsuno et al., "Plaque Assay of Neonatal Calf Diarrhea Virus and the Neutralizing Antibody in Human Sera", J. Clin. Microbiol., 5(1):1–4 (Jan., 1977) [Matsuno II].

"WHO News and Activities", Bull WHO, 67(5):583–587 (1989).

A. Kalica et al, "Identification of the Rotavirus Gene that Codes for Hemagglutination and Protease–Enhanced Plaque Formation", Virol., 125:194–205 (1983) [Kalica I].

A. Kalica et al, "Genes of Human (Strain Wa) and Bovine (Strain UK) Rotaviruses that Code for Neutralization and Subgroup Antigens", Virol., 112:385–390 (1981) [Kalica II].

H. Greenberg et al, "Rescue and Serotypic Characterization of Noncultivable Human Rotavirus by Gene Reassortment", Infec. and Immunol., 37(1):104–109 (Jul., 1982) [Greenberg I].

H. Greenberg et al, "Rescue of Noncultivatable Human Rotavirus by Gene Reassortment During Mixed Infection with ts mutants of a Cultivatable Bovine Rotavirus", Proc. Nat., Acad. Sci. USA, 78(1):420–424 (Jan., 1981) [Greenberg II].

R. Ward et al., "Serum–Neutralizing Antibody to VP4 and VP7 Proteins in Infants Following Vaccination with WC3 Bovine Rotavirus", J. Virol., 64(6):2687–2691 (Jun., 1990) [Ward I].

R. Ward et al, "Phenotype Mixing During Coinfection of Cells with Two Strains of Human Rotavirus", J. Virol., 62(11):4358–4361 (1988), Biological Abstracts, Abstract No. 87012291 [Ward II].

E. Wenske et al, "Genetic Reassortment of Mammalian Reoviruses in Mice", J. Virol., 56(2):613–616 (Nov., 1985).

I. Perez–Schael et al, "Clinical Studies of a Quadrivalent Rotavirus Vaccine in Venezuelan Infants", J. Clin. Microbiol., 28(3):553–558 (Mar., 1990).

O. Nakagomi et al., "Molecular Identification of a Novel Human Rotavirus in Relation to Subgroup and Electropherotype of Genomic RNA", J. Med. Virol., 28:163–168 (Jul., 1989) [Nakagomi I].

O. Nakagomi et al., "Identification of Rotavirus Genogroups by RNA–RNA Hybridization", Mol. and Cell Probes, 3:251–261 (1989) [Nakagomi II].

O. Nakagomi et al., "Genetic Analysis of a Human Rotavirus that Belongs to Subgroup I but has an RNA Pattern Typical of Subgroup II Human Rotaviruses", J. Clin. Microbiol., 25(7):1159–1164 (Jul., 1987) [Nakagomi III].

T. Nakagomi et al, "Relative Frequency of Human Rotavirus Subgroups I and II in Relation to Short and Long Electropherotypes of Viral RNA", Ann. Inst. Pasteur/Virol., 139:295–300 (Jul.–Sep., 1988).

A. Graham et al, "Reassortment of Human Rotavirus Possessing Genome Rearrangements with Bovine Rotavirus: Evidence for Host Cell Selection", J. Gen. Virol., 68:115–122 (Jan., 1987).

G. Losonsky et al, "Safety, Infectivity, Transmissibility and Immunogenicity of Rhesus Rotavirus Vaccine (MMU 18006) in Infants", Pediatr. Inf. Dis., 5(1):25–29 (Jan., 1986).

T. Vesikari et al, "A Comparative Trial of Rhesus Monkey (RRV–1) and Bovine (RIT 4237) Oral Rotavirus Vaccines in Young Children", J. Infect. Dis., 153(5):832–839 (May, 1986) [Vesikari I].

T. Vesikari et al., "Immunogenicity and Safety of Live Oral Attenuated Bovine Rotavirus Vaccine Strain RIT 4237 in Adults and Young Children", Lancet, 2:807–811 (Oct., 1983) [Vesikari II].

T. Vesikari et al, "Protective Efficacy Against Serotype 1 Rotavirus Diarrhea by Live Oral Rheusus–Human Reassortant Rotavirus Vaccines with Human Rotavirus VP7 Serotype 1 or 2 Specificity", Pediatr. Infect. Dis. J., 11(7):535–542 (Jul., 1992) [Vesikari III].

D. Chen et al, "Phenotypes of Rotavirus Reassortants Depend Upon the Recipient Genetic Background", Proc. Natl. Acad. Sci. US, 86:3743–3747 (May, 1989).

S. Urasawa et al, "Genetic Reassortment Between Two Human Rotaviruses Having Different Serotype and Subgroup Specificities", J. Gen. Virol., 67:1551–1559 (1986).

T. Urasawa et al, "Preparation of a Human Rotavirus Reassortant with Dual Serotype Specificity of VP3 of Serotype 4 and vp7 of Serotype 3", Sapporo Igaku Zasshi, 57(4):373–378, Biological Abstracts, Abstract No. 87033161 (1988).

A. Kapikian et al, "Development of a Rotavirus (RV) Vaccine by a Jennerian and a Modified Jennerian Approach", Modern Approaches to New Vaccines, Abstract (Sep., 19887) [Kapikian I].

A. Kapikian et al, "Antigenic Characterization of Human and Animal Rotaviruses by Immune Adherence Hemagglutination Assay (IAHA): Evidence for Distinctness of IAHA and Neutralization Antigens", Infect. and Immunol., 33(2):415–425 (Aug., 1981) [Kapikian II].

A. Kapikian et al, "Rotaviruses", Ch. 49 in Virology, 2d ed., pp. 1353–1363, ed. Field, Knipe et al, New York (1990) [Kapikian III].

L. Spence et al, "Comparison of Rotavirus Strains by Hemagglutination Inhibition", Can. J. Microbiol., 24:353–356 (1978).

M. Sabara et al, "Genetic Heterogenicity within Individual Bovine Rotavirus Isolates", J. Virol., 44(3):813–822 (Dec., 1982).

M. Liu et al, "Identification of the Simian Rotavirus SA11 Genome Segment 3 Product", Virol., 163:26–32 (1988).

G. Larralde et al, "Serotype–Specific Epitope(s) Present on the VP8 Subunit of Rotavirus VP4 Protein", J. Virol., 65(6):3213–3218 (Jun., 1991).

L. Bell et al, "Gastroenteritis Caused by Human Rotaviruses (Serotype Three) in a Suckling Mouse Model", Proc. Soc. Exp. Biol. and Med., 184:127–132 (1987).

S. Kitaoka et al, "Serologic Characteristics of a Human Rotavirus Isolate, AU–1, which has a 'Long' RNA Pattern and Subgroup I Specificity", J. Med. Virol., 23:351–357 (1987).

J. Gentsch et al, "Identification of Group A Rotavirus Gene 4 Types by Polymerase Chain Reaction", J. Clin. Microbiol., 30(6):1365–1373 (Jun., 1992).

S. Chiba et al, "Protective Effect of Naturally Acquired Homotypic and Heterotypic Rotavirus Antibodies", The Lancet, 130:417–421 (Aug., 1986).

D. Bernstein et al., "Protection from Rotavirus Reinfection: 2–Year Prospective Study", J. Infect. Dis., 164:277–283 (Aug., 1991).

G. Gerna et al, "Serotype 3 Human Rotavirus Strains with Subgroup I Specificity", J. Clin. Microbiol., 28(6):1342–1347 (Jun., 1990).

Y. Aboudy et al., "Use of Polyclonal and Monoclonal Antibodies and Analysis of Virus RNA in the Detection of Unusual Group A Human Rotaviruses", J. Med. Virol., 25:351–359 (1988).

ROTAVIRUS REASSORTANT VACCINE

CROSS-REFERENCE TO RELATED APPLICATIONS

This is a continuation-in-part of U.S. patent application Ser. No. 08/121,220, filed Sep. 14, 1990, now abandoned, which is a continuation of U.S. patent application Ser. No. 07/558,884, filed Jul. 26, 1990, now abandoned, which is a continuation-in-part of U.S. patent application Ser. No. 07/126,477, filed Nov. 30, 1987, now abandoned. This is also a continuation-in-part of U.S. patent application Ser. No. 08/249,696, filed May 26, 1994, now abandoned, which is a continuation of U.S. patent application Ser. No. 07/902,321, filed Jun. 22, 1992, now abandoned, which is a continuation-in-part of U.S. patent application Ser. No. 07/558,884, filed Jul. 26, 1990, now abandoned, which is a continuation-in-part of U.S. patent application Ser. No. 07/126,477, filed Nov. 30, 1987, now abandoned. These applications are incorporated by reference herein.

FIELD OF THE INVENTION

The present invention refers generally to novel rotavirus reassortants, vaccines employing the novel reassortants and methods for their preparation and administration.

BACKGROUND OF THE INVENTION

Rotaviruses are the single most important agent of acute gastroenteritis, a disease which requires hospitalization of infants and young children in developed countries, and a frequent cause of death in children less than 5 years of age in developing regions of the world. Studies in the United States, Australia, and Japan have demonstrated that between 34 and 63% of hospitalizations of children for acute diarrheal disease are associated with rotavirus infection [A. Z. Kapikian et al, *Rev. Infect. Dis.*, 2:459–469 (1980)]. The incidence of hospitalization for rotavirus gastroenteritis in a health maintenance organization in the U.S. was estimated to be 222 per 100,000 in children from 13 to 24 months of age, and 362 per 100,000 in those less than one year [W. Rodriguez et al, *Am. J. Dis. Child.*, 134:777–779 (1980)]. Infection with rotavirus was associated with 63% of all hospitalizations for acute diarrhea in this pediatric population [W. Rodriguez et al, cited above]. A recent review of mortality data in the U.S. from 1973 to 1983 indicated that 500 deaths per year occur in children less than 4 years old due to diarrheal diseases, and that 20 to 80% of excess winter deaths due to diarrhea in the U.S. are associated with rotavirus infections [M.-S. Ho et al, *JAMA*, 260:3281–3285 (1988)]. Rotaviruses are also responsible for a substantial proportion of the mortality associated with diarrheal diseases in third world countries. An effective rotavirus vaccine would therefore have a major impact on the health of children in both the developed and developing areas of the world.

Rotaviruses have an inner and outer capsid with a double-stranded RNA genome formed by eleven gene segments. Multiple serotypes have been defined by plaque reduction neutralization tests, and studies of reassortant viruses have demonstrated that two outer capsid proteins, v.p.7 and v.p.4, are the determinants of virus serotype. The v.p.7 protein is coded for by either gene segment 7, gene segment 8 or gene segment 9 of the particular human rotavirus. The location of the v.p.7 encoding gene may be determined for each specific rotavirus by conventional experimental methods. The protein v.p.4 is an 88,000 dalton major surface structural protein product of gene 4 of a rotavirus. Like v.p.7, it functions as a major serotype-specific antigen, operative in serum neutralization (SN) tests, capable of inducing serotype-specific neutralizing antibody, and capable in a mouse system of inducing serotype specific immune protection against rotavirus disease. [See. Offit et al. (1986) supra]. In some earlier references. the v.p.4 was referred to as v.p.3. After 1988. a change in nomenclature. resulted in the more proper reference to this protein as v.p.4 [M. Liu et al. *Virol.*, 163:26–32 (1988) and M. K. Estes et al. *Immunol. Invest.*, 18:571–581 (1989)].

Since the gene segments encoding the v.p.7 and v.p.4 proteins segregate independently [Y. Hoshino et al, *Proc. Natl. Acad. Sci. USA*, 82:8701–8704 (1985) and P. Offit et al, *J. Virol.*, 57:376–378 (1986)]. it has been proposed that serotyping nomenclature include both the G type. determined by v.P.7. and the P type. determined by v.p.4 [M. Estes et al, *Microbiological Reviews*, 53:410–449 (1989)]. Most human rotavirus infections in the U.S. are caused by viruses of G types 1. 2. 3. or 4. and P types 1. 2. or 3 [V. Gouvea et al. *J. Infect. Dis.*, 162:362–367 (1990). P. Woods et al. *J. Clin. Microbiol.*, 30:781–785 (1992). and J. Gentsch et al. *J. Clin. Microbiol.*, 30:1365–1373 (1992)]. However. other human rotavirus types. including for example. type G9. are more prevalent in Asia. Europe and certain third world countries.

A number of animal rotaviruses are attenuated in humans. and have been evaluated as potential live rotavirus vaccines. including the bovine serotype G6 WC3 rotavirus. The WC3 vaccine virus was shown to be immunogenic and non-reactinogenic in infants [H. F. Clark et al. *American Journal Diseases of Children*, 140:350–356 (1986) and H F. Clark et al. *J. Infect. Dis.*, 158:570–587 (1988)]. but was inconsistent in providing protective immunity against human rotavirus infection [H. F. Clark et al, *J. Infect. Dis.*, 158:570–587 (1988). D. Bernstein et al, *J. Infect. Dis.*, 162:1055–1062 (1990). and M. Georges-Courbot et al. *Res. Virol.*, 142:405–411 (1991)]. However. it has been proposed that serotype-specific immunity is necessary to induce consistent protection against rotavirus diarrhea [J. Flores et al. *Lancet*, 1:882–884 (1987) and C. Christy et al. *Pediatr. Infect. Dis.*, 7:645–650 (1988 )].

There exists a need in the art for effective vaccines providing protective immunity against rotavirus infection and the severe clinical symptoms associated therewith.

SUMMARY OF THE INVENTION

The present invention provides rotavirus reassortants useful as safe and efficacious vaccines for preventing human rotavirus infection and the clinical symptoms associated with severe rotavirus disease.

In one aspect the invention provides a rotavirus reassortant derived from human and non-human rotavirus parental strains. which reassortant contains from a human rotavirus parental strain at least the gene (or gene segment) encoding the virion surface protein v.p.7 neutralization antigen. The non-human gene segments of the reassortant are preferably provided by the WC3 bovine rotavirus strain or progeny thereof.

In another aspect the invention provides a rotavirus reassortant containing from a human rotavirus parental strain at least the gene encoding the v.p.4 neutralization antigen. The non-human gene segments are preferably provided from the WC3 bovine rotavirus parental strain or progeny thereof.

As another aspect of this invention there is provided a vaccine for providing immunological protection against acute diarrhea caused by human rotavirus which contains at least one of the novel rotavirus reassortants of the present invention. One particularly preferred univalent vaccine of the invention comprises the reassortant WI79-3,9 (serotype G1). Particularly desirable vaccines contain the reassortant WI79-3,9 in combination with at least one other rotavirus reassortant selected from a G2, G3, G4, P1 and P2 rotavirus reassortant of the invention.

Another aspect of the invention provides a method of vaccinating humans against human rotavirus infection employing the reassortant vaccines of the invention. This vaccination method may also employ more than one of the vaccine compositions of this invention.

Other aspects and advantages of the present invention will be apparent upon consideration of the following detailed description of the invention, including illustrative examples of the practice thereof.

DETAILED DESCRIPTION OF THE INVENTION

This invention involves rotavirus reassortants suitable for use as vaccines, which are characterized by safety to humans and the ability to confer immune protection against human rotavirus infection. The reassortants are produced by genetic reassortment between an attenuated bovine rotavirus (preferably WC3 or progeny thereof) and at least one rotavirus representing an epidemiologically important human serotype. In one embodiment of this invention, the human rotavirus contributes to the reassortant at least the gene segment encoding the v.p.7 protein. In another embodiment of this invention, the human rotavirus parent contributes to the reassortant at least the gene segment encoding the v.p.4 protein. In still a further embodiment, the human rotavirus parental strain contributes at least both the v.p.7 and v.p.4 gene segments. In additional embodiments, the human rotavirus parental strain may contribute gene segments in addition to those which encode the v.p.7 and/or v.p. 4 antigens.

The human rotavirus gene which encodes for the neutralization antigen v.p.7 and/or v.p.4 in the novel reassortant may be selected from any human rotavirus serotype for which immunization is desired. Desirably, in a reassortant of this invention the v.p.7 gene is derived from a G1, G2, G3, or G4 human rotavirus serotype and the v.p.4 protein is derived from a human P1 or P2 serotype. Among the rotavirus strains noted to be clinically significant in human rotavirus infections (hereinafter "human rotavirus strains"), including strains useful in the present invention, are the strains provided below:

serotype G1: WI79, Wa, D;
serotype G2: strains WISC2 and DS1;
serotype G3: strains WI78, P, HCR3A;
serotype G4: Bricout (Br) B, ST3;
serotype G8: 69M;
serotype G9: WI61;
serotype P1: WI79, WI78, WI61, Wa;
serotype P2: DS1; and
serotype P3: WISC2; BrB; BrA, M37.

Rotavirus DS-1 was deposited on Dec. 13, 1996 with the American Type Culture Collection, 12301 Parklawn Drive, Rockville, Md., U.S.A. for patent purposes under the terms of the Budapest Treaty. This deposit is identified by ATCC Accession Number VR 2550. Rotavirus WI61 was deposited on Dec. 13, 1996 with the American Type Culture Collection, 12301 Parklawn Drive, Rockville, Md., U.S.A. for patent purposes under the terms of the Budapest Treaty. This deposit is identified by ATCC Accession Number VR 2551.

This list of human rotavirus strains is non-exclusive. For example, several rotavirus strains previously identified in animal infections have also been found in human infections. These strains may be anticipated to be useful as 'human' rotavirus strains for the purposes of this invention, e.g., the 'porcine' rotavirus OSU, a serotype G5, and the 'bovine' rotavirus B223, a serotype G10. One of skill in the art may readily obtain other appropriate human strains from suitable depositaries or academic or commercial sources. Alternatively, other suitable human rotavirus strains may be isolated and adapted to growth on a suitable cell line, e.g. MA104, Vero cells, or the like, using known techniques. See, e.g., Clark et al (1987) (describing isolation of WI61 strain) and Example 1.

The non-human genes present in the reassortants of this invention are obtained preferably from the attenuated, serotype G6, bovine rotavirus strain WC3 or its progeny, described in detail in U.S. Pat. No. 4,636,385. The disclosures of that patent are incorporated by reference herein to provide additional information about this rotavirus strain. WC3 replicates to a high titer in CV-1 cells (ATCC CCL70) and in Vero cells (ATCC CCL-81) and is known to be attenuated and immunogenic in human infants [Clark et al, *Amer. J. Dis. Children*, 140:350 (1986)].

Representative isolates of this strain type which may be substituted for WC3 are WC2, WC4, WC5, WC6, WC7, WC8, WC9 and WC10. These bovine rotaviruses are readily distinguishable from other strains of bovine rotavirus by their distinctive RNA electropherotype, their failure to hemagglutinate primate red blood cells, their plaque morphology and response in the SN test.

Particularly desirable reassortants provided by the present invention contain the gene encoding the v.p.7 protein contributed by the selected human rotavirus. The selected human rotavirus may also be attenuated, if desired, for use in the reassortant. The gene encoding the v.p.4 protein may be contributed by attenuated bovine rotavirus WC3 or by the human rotavirus. The remaining gene segments are contributed by either the human or animal parental rotavirus, or both.

Throughout the specification, specific reassortants are designated by reference to the human strain which designates the gene or genome segment (aka gene segment) encoding the v.p.7 or v.p.4 protein antigen. Following this human parental strain, e.g. WI79, the confirmed human gene segments present in the bovine WC3/human rotavirus reassortant are identified by segment number. For example, reassortant WI79-3,9 contains human gene segments 3 and 9 from strain WI79. Originally this reassortant was designated WI79-9 to indicate that it contained the WI79 v.p.7 encoding gene segment. The presence of human WI79 gene segment 3, which runs closely between the human and bovine strains on the gels, was confirmed via polymerase chain reaction (PCR). However, gene 3 from WI79 was always present in this reassortant which was deposited on Nov. 25, 1987 with the American Type Culture Collection (ATCC), 12301 Parklawn Drive, Rockville, Md. 20852 (U.S.A.). (See Table 1 below).

Alternatively, a rotavirus reassortant of this invention may be constructed which contains genes from more than one parental human rotavirus strain, as well as from the bovine rotavirus parental strain. One example of such a reassortant is WI79-3+WISC2-9, which contains gene segment 3 from WI79 and gene segment 9 (which encodes the v.p.7 antigen) from strain WISC2, as well as the bovine gene segments.

Table 1 below provides examples of particularly desirable reassortants containing the human v.p.7 gene segment and/or the human v.p. 4 gene segment. These reassortants are listed in association with their G or P serotype in the order of their present desirability as representatives of that serotype. As indicated in Table 1, many of the reassortants and parental rotavirus strains were deposited with the American Type Culture Collection (ATCC), 12301 Parklawn Drive, Rockville, Md. 20852 (U.S.A.), an accepted Depositary Authority as indicated, on the dates specified above and were given ATCC designations upon viability testing.

TABLE 1

| Human Serotype | Parent or Reassortant | ATCC # | Deposit Date |
|---|---|---|---|
| G1 | WI79-3,9[a] | VR2194 | Nov. 25, 1987 |
|    |          | VR2196 | Nov. 25, 1987 |
|    | WI79-4,9 | VR2415 | July 8, 1993 |
| G2 | WI79-3 + WISC2-9 | VR2493 | Dec. 7, 1994 |
|    | WISC2 parental strain | VR2417 | July 8, 1993 |
| G3 | WI78-8 | VR2494 | Dec. 7, 1994 |
|    | WI78-1,6-11 | VR2195 | Nov. 25, 1987 |
|    | WI78-1,7-11[b] | | |
| G4 | Bricout B-9 | VR2492 | Dec. 7, 1994 |
| P1 | WI79-4 | VR2377 | June 19, 1992 |
|    | WI79-4,9 | VR2415 | July 8, 1993 |
|    | WI61-4[b] | | |
| P2 | DS1-4[b] | | |

[a]Originally named WI79-9. The two deposits represent different passage levels of the reassortant.
[b]Not deposited.

The deposits of WI79-3,9 and WI78-1,6-11 have been converted to comply with the requirements of the Budapest Treaty. All other deposits have been originally made under the Budapest Treaty. All restrictions on the availability to the public of the deposited material identified in Table 1 will be irrevocably removed upon the grant of a patent on this application, the culture(s) will be maintained for a period of 30 years from the deposit date, or at least five years after the most recent request for a sample, whichever is longer; and the deposit will be replaced if viable samples cannot be dispensed by the depositary. During the pendency of this patent application, access to these deposits will be afforded to one determined by the Commissioner to be entitled thereto.

Production of Reassortants

The method for producing the novel reassortants of this invention includes the step of isolating the human and other species parent rotavirus by culturing in a suitable cell culture. Briefly, the parent viruses are used to co-infect a cell line by conventional techniques and the progeny viruses are identified by running each parent and the progeny on conventional gel electrophoresis. The parental viruses may be either two rotavirus strains (e.g. Bricout B and WC3), or a rotavirus strain and a selected reassortant (e.g. WISC2 and WI79-3,9). Each gene segment runs with a characteristic mobility. The makeup of the reassortant is readily identified by comparison of its electropherotype profile with that of the parent. Performing the infections and gel electrophoresis techniques to obtain such reassortants are skills known to the art. The isolation technique is standard and is described in more detail in Example 1.

Suitable cells for such isolation and infection include primate VERO cells (ATCC CCL-81), African green monkey kidney cells CV-1 (ATCC CCL-70); BSC-1 (ATCC CCL-26). Preferably, fetal green monkey cell MA-104, and primary primate kidney cell cultures are utilized. Vero cells are presently preferred for vaccine manufacture. For purposes of this invention, primary primate kidney cell cultures include first, second (secondary) or third (tertiary) passages of kidney cells derived from the indicated species of primate. Each of these cell culture substrates may be grown in BHK medium [MacPherson, I. and M. Stoker, *Virology*, 16:147 (1962)], supplemented with 10% fetal calf serum, Eagle's minimal essential medium with 10% fetal calf serum, or medium 199 with 10% fetal calf serum. These media may also contain gentamicin, 25 micrograms per milliliter. These cell lines may be used alone, or in alternate passages of the viruses. When used in combination, a separate but different cell line can be used in each of the various passages of the virus.

For example, a suitable cell culture is infected with both the attenuated bovine rotavirus strain WC3 and the desired human serotype rotavirus. Alternatively, a suitable cell culture may be infected with the desired human parental strain and a human/WC3 reassortant of the invention. Mixed infections are designed to maximize the potential for reassortment by ensuring that large and equal concentrations of each parent virus are replicating simultaneously. After infection and sufficient time and conditions for gene reassortment, reassortant progeny clones are examined by random selection of plaques, e.g., by performing a plaque assay of the virus yield from the mixed infection. The virus is propagated in individual plaques which are induced by inoculation of the yield of the mixed infection onto another cell culture monolayer.

Polyacrylamide gel electrophoresis with silver stain (PAGE-SS) according to the procedure of Dolan et al, *J. Clin. Microbiol.*, 21:753 (1985) is employed to analyze each such virus population and compare its electropherotype with that of each parental rotavirus. The identity of genes which run closely (e.g., in certain human and bovine strains, gene segment 3 runs very closely on electropherotype gels), may optionally be confirmed via known polymerase chain reaction techniques [J. Gentsch et al, *J. Clin. Microbiol.*, 30:1365–1373 (1992); V. Gouvea et al, *J., Clin. Microbiol.*, 28:276–282 (1990)].

The proportion of rotavirus reassortants isolated may be enhanced by selecting plaques whose morphology differs from that of either parent. Alternatively, progeny clones may be selected from the virus yield of the mixed infection after treatment with hyperimmune antiserum to the serotype of the rotavirus which does not contribute the desired protein antigenen-coding gene [See, e.g., the method of U.S. Pat. No. 4,571,385], prior to performing the plaque analysis of the population. This method may be applied to any human or animal virus.

Progeny clones are examined by harvesting individual plaques, which are then cultivated individually in cell culture and examined for their gene constitution by PAGE-SS. Reassortant progeny clones are selected as vaccine candidates if their PAGE-SS reveals the presence of at least the gene coding for the surface antigen v.p.7 from the human rotavirus against which immune protection is being sought, or the gene coding for the surface antigen v.p. 4 from the human rotavirus against which immune protection is being sought. Preferably, the PAGE-SS will reveal the presence of human v.p.7 in the reassortant. Alternatively, where desired, the PAGE-SS will reveal the presence of the human v.p.4 in the reassortant, or both the v.p.4 and v.p.7 encoding gene segments from the human rotavirus parental strain. Other human genes may also be found in the reassortant.

Vaccine Compositions

Vaccines for providing immunological protection against acute diarrhea caused by human rotavirus infection may contain one or more of the novel reassortants of the present invention. Desirable vaccine compositions listed in order of from presently most preferred to presently lesser preferred compositions are summarized in Table 2 and discussed in detail below.

TABLE 2

| Vaccine Compositions | Preferred Reassortants |
|---|---|
| G1 + G2 + G3 + G4 | WI79-3,9 + (WI79-3 + WISC2-9) + WI78-8 + BrB-9 |
| G1 + G2 + G3 + G4 + P1 | WI79-3,9 + (WI79-3 + WISC2-9) + WI78-8 + BrB-9 + WI79-4 |
| G1 + G2 + G3 + P1 | WI79-3,9 + (WI79-3 + WISC2-9) + WI78-8 + WI79-4 |
| G1 + P1 | WI79-3,9 + WI79-4 |
| G1 + G2 + G3 | WI79-3,9 + (WI79-3 + WISC2-9) + WI78-8 |
| G1 + G2 + G3 + G4 + P1 + P2 | WI79-3,9 + (WI79-3 + WISC2-9) + WI78-8 + BrB-9 + WI79-4 + DS1-4 |
| G1 | WI79-3,9 |

One such vaccine, a univalent vaccine, contains a single G1 rotavirus reassortant. Preferably, this G1 reassortant is WI79-3,9 which has been shown to be effective in preventing rotavirus gastroenteritis during a subsequent epidemic of predominantly serotype G1 rotavirus. This reassortant was also the subject of study provided in detail in Example 5. Briefly, the study was prospective, randomized, double-blind, placebo-controlled study performed, conducted over a single rotavirus season in a total of 325 infants who were aged 2-8 months at enrollment. The subjects were randomized to receive either placebo or WI79-3,9 virus vaccine at $10^{7.3}$ plaque forming units in three oral doses each separated by 2 months and followed for seven days after each dose for occurrence of adverse events and during the subsequent winter for development of rotavirus gastroenteritis. It was found that administration of WI79-3,9 virus vaccine was well tolerated, and rates of adverse events including fever were similar in vaccine and placebo recipients. The live, attenuated serotype G1 bovine-human rotavirus reassortant WI79-3,9 vaccine was found safe and effective in prevention of homotypic human rotavirus infection in infants. See Example 5 below.

The vaccine compositions of the invention may desirably include other rotavirus reassortants of the invention, in addition to a G1 reassortant. Preferably, these reassortants are representative of one or more of serotypes G2, G3, G4, P1, and P2, as listed above in Tables 1 and 2. For example, in one desirable formulation, the invention provides a vaccine composition containing WI79-3,9 and WI79-4 (serotype G1 and P1, respectively). This composition has been shown to elicit a stronger immune response than does a single reassortant rotavirus containing both the human v.p.4 and the human v.p.7 (encoded by gene segment 9). See Example 6 below.

Other suitable combinations include a quadrivalent vaccine containing a G1 reassortant of the invention in combination with a G2, G3, and P1 reassortant, e.g. WI79-3,9; WI79-3+WISC2-9; WI78-8; and WI79-4. See Example 7 below in which preliminary analysis of such a vaccine reveals greater than 70% efficacy.

Suitable combination vaccines, which may be univalent, bivalent, trivalent, quadrivalent, quinquavalent or hexavalent may include various combinations of the G1, G2, G3, G4, P1 and P2 reassortants. Other suitable reassortants of the invention may be selected for use in vaccine compositions other than those specified in Table 2 by reference to Table 1 above and the present specification.

The vaccines of the invention contain conventional carriers. Suitable carriers are well known to those of skill in the art. These vaccine compositions are preferably prepared in liquid unit dose forms. Other optional components, e.g. stabilizers, buffers, preservatives, excipients and the like, may be readily selected by one of skill in the art. However, the compositions may be lyophilized and reconstituted by the attending physician prior to administration of the dose. Alternatively, the vaccine compositions may be prepared in any manner appropriate for the chosen mode of administration, e.g. parenteral. The preparation of a pharmaceutically acceptable vaccine, having due regard to pH, isotonicity, stability and the like, is within the skill of the art.

When adapted for oral administration, one particularly desirable formulation includes as a carrier Williams E media/50% sucrose/0.1M succinate/50 mM phosphate liquid. Another desirable formulation includes 0.2M succinate and 0.1M phosphate. When adapted for parenteral administration, conventional adjuvants may also be employed in the vaccine composition, e.g., aluminum hydroxide.

Optionally, the vaccine may be formulated to contain other active ingredients and/or immunizing antigens. For example, when adapted for oral administration, formulation with the Sabin polio vaccine may be desirable.

The dosage regimen involved in a method for vaccination, including the timing, number and amounts of booster vaccines, will be determined considering various hosts and environmental factors, e.g. the age of the patient, time of administration and the geographical location and environment.

Method of Vaccination

Therefore, also included in the invention is a method of vaccinating humans against human rotavirus infection with the novel reassortants and vaccine compositions described above. The vaccine compositions including one or more of the reassortants described herein are administered, preferably by the oral route, in a suitable dose, preferably liquid. The vaccine may also be administered intranasally or parenterally. Alternatively, the vaccine may be administered to nursing mothers as a means for transferring immunity to the infant.

The dosage for all routes of administration is generally greater than $10^6$, between $10^6$ and $10^9$ plaque forming units (pfu) of the reassortant, with the preferred dosage being $10^7$ pfu. Additional doses of the vaccines may also be administered. It may be preferable to inoculate susceptible infants and children on an annual basis prior to the "rotavirus season". Rotavirus infection in humans has been observed to occur in various geographical regions during the same season, e.g. in winter in the United States. Repeated inoculations prior to that season for susceptible infants and children may be indicated. For example, one currently preferred dosage regimen for the U.S. includes three doses approximately two months apart prior to the beginning of the rotavirus season.

The following examples illustrate the preferred methods for preparing the rotavirus reassortant vaccines of the invention. These examples are illustrative only and do not limit the scope of the invention.

EXAMPLE 1

Isolation of the Rotaviruses

The bovine rotavirus strain WC3 and human rotavirus strains used in producing reassortants according to the invention were isolated in cell line MA104 or in primary primate cells and then adapted to growth in the Vero cell line.

The human origin rotaviruses were isolated by standard techniques as described previously for isolation of human rotavirus strain WI61 in Clark et al (1987) supra. Stools of infants ill with gastroenteritis were determined to contain rotavirus by ELISA and/or by the PAGE-SS technique for detection of the rotavirus-characteristic 11 segments of double-stranded RNA. Rotavirus-containing stools were emulsified into a 5% (w/v) suspension in serum-free Eagle's Minimal Essential Medium containing 500 units of penicillin/ml, 500 micrograms of streptomycin/ml, 40 micrograms of gentamicin/ml 50 units of nystatin/ml, and 20 micrograms of trypsin/ml. The stool suspension was clarified by centrifugation at 2000×g for 30 minutes.

Clarified supernatant fluid was incubated with an equal volume of purified trypsin (10 microgram/ml) in phosphate buffered saline (PBS) for 60 minutes at 37° C. The trypsin-treated stool supernatant fluid was inoculated in a volume of 0.2 ml into tube cultures of MA104 cells which had previously been washed three times with PBS. After absorption of this rotavirus-containing fluid for 30 minutes at 37° C., the tube cultures were fed with 1.5 ml of Sato medium containing 1 microgram/ml of purified trypsin and incubated in a roller apparatus at 37° C.

Inoculated cell cultures were harvested after seven days of incubation by freezing and thawing of the combined cells and cell culture medium. Serial passage was accomplished by inoculating 0.2 ml of undiluted cell culture suspension into fresh tubes of MA104 cell culture treated in the same manner as the initial passage inoculated with stool suspension supernatant fluid. Cell culture suspensions from each successive passage were analyzed for the presence of rotavirus RNA by the PAGE-SS technique. Detectable concentrations of rotavirus RNA were usually obtained by the second and third passage level. Visible cytopathic effect (CPE) usually appeared by the second to fifth cell culture passage.

After the rotavirus strain has become cytopathic, serial passages were made whenever CPE involved more than 75% of the cell monolayer (2 to 7 days). When a rotavirus isolate consistently induced CPE in roller tube cultures within 48 hours (usually within 4 to 8 passages), serial passage was performed in stationary cultures of MA104 cells fed with BHK medium supplemented with 13 micrograms/ml of unpurified trypsin (Flow Labs). Serial subculture in MA104 cell stationary cultures was performed in the same manner as that used for roller tubes, and was continued until the isolated rotavirus was determined to efficiently induce plaques under agarose overlay in MA104 cell culture.

When the rotavirus isolate efficiently induces plaques in the plaque induction assay according to Offit et al, *J. Virol. Methods*, 7:29 (1983) [usually $10^5$ to $10^7$ pfu per ml], it has adapted to growth in the MA104 cell culture. It is then adapted to growth in stationary cultures of CV-1 cells by similar serial passage methods, except that the medium is Eagle's MEM serum-free, containing 6.25 microgram/ml unpurified trypsin (Flow). At varying passage levels, as appropriate, the isolated rotavirus may be genetically purified by isolation and propagation of a single plaque produced in MA104 cell culture. Mechanical aspiration of cells within a single plaque, well separated from any surrounding plaques is followed by serial propagation of virus contained in this cell suspension by standard technique.

It is presently preferred to inoculate the virus into tube cultures of Vero cells in the presence of serum-free medium with 0.75 μg/ml purified trypsin. These cultures are incubated in roller apparatus at 37° C., with the trypsin being replenished at 3 to 4 day intervals. The culture is harvested by freezing and thawing about 7 to 10 days after inoculation. Subpassages are made in additional roller tubes of Vero cells or stationary cultures of Vero cells in tissue culture flasks. After 2–5 passages, virus is capable of causing CPE in stationary cultures, and may be used to prepare the vaccines.

The identity of the cell culture-adapted rotavirus compared with the virus in the original stool suspension is confirmed by comparison of the RNA electropherotypes induced in polyacrylamide gel. The serotype of each cell culture-adapted rotavirus may be determined by reaction with serotype-specific hyperimmune antisera to prototype rotaviruses prepared in rabbits and guinea pigs [Clark et al, (1987) supra].

EXAMPLE 2

Producing the Reassortants

A. WI79-3,9, WI79-4 and WI79-4,9

MA104 cell culture in a 24 well plate was washed twice with PBS and inoculated with 0.2 ml of a suspension containing $2.0\times10^5$ pfu of human serotype 1 strain WI79 rotavirus (WI79 was passaged eleven times in MA104 cells, including two plaque purifications, and thirteen times in CV-1 cells). This virus was allowed to absorb to cells for 60 minutes at 37° C., after which the virus was removed and the cells washed twice with PBS. 0.2 ml of a suspension containing $4.0\times10^1$ pfu of WC3 rotavirus (passage level 12) was added. The WC3 rotavirus was allowed to absorb for 60 minutes, after which the cells were washed three times with PBS and fed with 1.5 ml of BHK medium with 13 micrograms/ml trypsin was added. Infected cells were incubated at 37° C. until CPE involved the entire monolayer (approximately 96 hours post infection).

The mixed infection was then harvested by three cycles of freezing and thawing. The cell culture fluids comprising this harvested infection were then reacted in a neutralization reaction consisting of addition of cell culture fluids to an equal volume of hyperimmune rabbit antiserum to bovine serotype 6 rotavirus, obtained by conventional means and diluted 1:50. The resulting neutralization mixture was then incubated at 37° C. for 30 minutes, after which the surviving virus was plagued on MA104 cell culture by standard technique. Plaques induced in MA104 cell culture were harvested at random, propagated in MA104 cell culture, and analyzed by PAGE-SS for dsRNA electropherotype in comparison with parental rotaviruses WC3 and WI79.

Among these plaque isolates was a rotavirus reassortant which was deposited in two different passages on Nov. 25, 1987 with the ATCC and designated VR2194 and VR2196. This WC3/WI79 bovine/human rotavirus reassortant designated WI79-3,9 (originally WI79-9), contains gene 3 and 9 from the human G1 serotype rotavirus WI79. Originally this reassortant was designated WI79-9 to indicate that it contained the WI79 v.p.7 encoding gene segment. The presence of human WI79 gene segment 3, which runs closely between the human and bovine strains on the gels, was confirmed via polymerase chain reaction (PCR). However, gene 3 from WI79 was always present in the reassortant as deposited.

WI79-3,9 was antigenically bivalent in virus neutralization (VN) tests with hyperimmune antisera. It reacts with antisera to bovine serotype and human G1 rotaviruses. WI79-3,9 rotavirus reassortant replicates to a titer of $10^{7.0}$ pfu/ml in CV-1 cell culture. At this concentration, it was completely attenuated for orally inoculated adults and infants as young as two months of age. In a high percentage of infants, WI79-3,9 rotavirus reassortant induced virus neutralizing (VN) antibody specific for rotavirus G1 and/or the bovine rotavirus serotype.

WC3/WI79 bovine/human rotavirus reassortant WI79-4, containing gene 4 from WI79 was also identified in this manner. WI79-4 was similarly neutralized by antisera to human P1 rotavirus and by antisera to bovine rotavirus.

To generate WC3/WI79 bovine/human rotavirus reassortant WI79-4,9, which contains gene segments 4 and 9 (v.p.4 and v.p.7) from the human rotavirus strain WI79, reassortants WI79-3,9 and WI79-4 were combined in a culture and treated with anti-bovine rotavirus serum. WI79-4,9 was then identified among the progeny and harvested from the culture. It contained neither the v.p.4 or v.p.7 antigens from the bovine strain. WI79-4,9 was not neutralized at all by bovine antisera, even though it contains nine bovine genes. It was neutralized by antisera to human type G1.

B. WI61-4 and WI61-7,9

MA104 cell culture in a 24 well plate was washed twice with PBS and inoculated with 0.2 ml of a suspension containing $2.0 \times 10^5$ pfu of human strain WI61 rotavirus (WI61 was passaged eleven times in MA104 cells, including two plaque purifications, and thirteen times in CV-1 cells). This virus was allowed to absorb to cells for 60 minutes at 37° C., after which the virus was removed and the cells washed twice with PBS. 0.2 ml of a suspension containing $4.0 \times 10^1$ pfu of WC3 rotavirus (passage level 12) was added. The WC3 rotavirus was allowed to absorb for 60 minutes, after which the cells were washed three times with PBS and 1.5 ml of BHK medium with 13 micrograms/ml trypsin was added. Infected cells were incubated at 37° C. until CPE involved the entire monolayer (approximately 96 hours post infection).

The mixed infection was then harvested by three cycles of freezing and thawing. The cell culture fluids comprising this harvested infection were then reacted in a neutralization reaction consisting of addition of cell culture fluids to an equal volume of hyperimmune rabbit antiserum to bovine serotype rotavirus, obtained by conventional means and diluted 1:50. The resulting neutralization mixture was then incubated at 37° C. for 30 minutes, after which the surviving virus was plaqued on MA104 cell culture by standard technique. Plaques induced in MA104 cell culture were harvested at random, propagated in MA104 cell culture, and analyzed by PAGE-SS for dsRNA electropherotype in comparison with parental rotaviruses WC3 and WI61.

Among these plaque isolates was a WC3/WI61 bovine/human rotavirus reassortant designated WI61-4, containing gene 4 (v.p. 4) from human strain WI61. Also identified in this manner was WC3/WI61 bovine/human rotavirus reassortant WI61-7,9 containing genes 7 and 9 (v.p. 7) from WI61.

C. WI79-3+WISC2-9

Reassortant WI79-3+WISC2-9, which contains human gene 3 from WI79 and human gene 9 (encoding the human v.p.7 antigen) from WISC2 was prepared using the methods described above. This reassortant was the result of a mixed infection of WI79-3,9 and WISC2. The reassortant was selected for the presence of human gene segment 9 from WISC2 via electrophoretic gel. The presence of human gene segment 3 from WI79 was later confirmed via PCR analysis.

EXAMPLE 3

Method for Making WI79-3,9 Vaccine

Rotavirus reassortant WI79-3,9 was passaged a total of six times in MA104 cell culture which included three serial plaque purifications and then was adapted to growth in CV-1 culture by three passages in CV-1 cells. The third CV-1 cell passage represents a test vaccine evaluated in adult volunteers and infants. For the vaccine trial provided in Example 6, this material was used as a seed pool for a vaccine lot propagated in CV-1 cells, manufactured by Program Resources, Inc. (Rockville, Md.). Vero cells may also be used.

The test vaccine was produced in a manner similar to that used for WI78-1,6-11 in part A, above. Roller bottles (850 cm$^2$) of CV-1 cells were infected with WI79-3,9 rotavirus reassortant at a M.O.I. of approximately 0.30. Virus was adsorbed for thirty minutes at 37° C., after which the cell cultures were fed with 100 ml/roller bottle of BHK medium, serum-free, containing 25 micrograms/ml gentamicin and 1.0 microgram/ml purified trypsin (Sigma Chemical Company). Infected cell cultures were incubated at 37° C. and harvested when CPE involved the entire monolayer at 72 hours post-infection.

Sterility tests consisted of inoculation of the vaccine into standard laboratory media for the culture of aerobic and anaerobic bacteria, mycobacteria, and fungi. The vaccine was tested for mycoplasma by inoculation of 3T3 mouse cells in culture, followed by staining with Hoechst stain for intracytoplasmic DNA. Testing for adventitious viruses included inoculation of human and primate cell cultures in the presence of serotype-specific anti-rotavirus serum obtained by conventional methods, to suppress the replication of vaccine virus, which were observed for the appearance of CPE and/or hemadsorption. Adult and newborn mice were inoculated intracerebrally and orally with the vaccine and observed subsequently for 30 days. Adult guinea pigs were inoculated intraperitoneally and observed for 15 days post-inoculation.

Infectious rotavirus reassortant WI79-3,9 vaccine had an infectivity titer of $10^{7.5}$ pfu/ml. The vaccine stock has been deposited with the American Type Culture Collection, as ATCC No. VR2196.

EXAMPLE 4

Administration of WI79-3,9 Vaccines

Administration of vaccine to adults: Four adult volunteers were given a full dose ($10^{7.5}$ pfu) of WI79-3,9 vaccine orally after oral administration of 30 ml of MAALOX® to buffer stomach acids. All adults remained clinically normal. None shed vaccine rotavirus in stool samples collected three days post infection.

Administration of vaccine to infants: WI79-3,9 vaccine was administered orally to infants in a volume of 2.5 ml, including 2.0 ml of vaccine and 0.5 ml of cherry syrup. Infants were given 30 ml of infant formula, or occasionally 1 ml/kg body weight of MAALOX® 30 minutes prior to vaccine to buffer stomach acids. In sequence, two infants were given a WI79-3,9 dose of $10^{5.5}$ pfu; two were given a dose of $10^{6.5}$ pfu; and 49 infants and one three year old child were given a dose of $10^{7.5}$ pfu. No vaccine associated symptoms of disease were observed. Four of 50 infants given a full dose shed detectable levels of vaccine virus in stool. 30 of 54 infants, or 57%, given any dose of vaccine developed a virus-neutralizing serum antibody response to one or more of rotavirus serotypes G1, G3, or bovine. This immune response to a primary dose of WI79-3,9 was most often directed against the bovine serotype of rotavirus, WC3, or serotype G1, WI79, reflecting the dual antigenic constitution of the rotavirus reassortant.

The efficiency of induction of an immune response to WI79-3,9 in infants could be further enhanced by giving a second "booster" dose of vaccine orally, 30 days after the primary dose. Such a booster could consist of the WI79-3,9 reassortant virus used for the original inoculation or a vaccine consisting of either virus parent to the WI79-3,9 reassortant. The combined results with the WI79-3,9 virus vaccine followed by any of the three booster doses gave a 71% incidence of serum antibody response in 2 to 4 month old infants and 91% in 5 to 11 month old infants. Following a booster dose, heterotypic antibody to serotype G3 (SA11) rotavirus was also induced with a frequency similar to that obtained to bovine serotype or with serotype G1 rotavirus. Thus, antibody was induced to the two serotypes, G1 and G3, most often responsible for rotavirus disease in infants in the United States.

Additional studies of this vaccine are described in detail in H. F. Clark et al, *J. Infect. Dis.*, 161:1099–1104 (1990) and H. F. Clark et al, *Vaccine*, 8:327–333 (1990). Both references are incorporated herein by reference.

EXAMPLE 5

WI79-3,9 Vaccine Trial

A total of 325 infants were enrolled in the study, 237 in Rochester, and 88 in Philadelphia. Randomization was conducted at a 2:1 ratio of vaccine to placebo in Rochester, and at a 1:1 ratio in Philadelphia, so that 207 infants received vaccine and 118 received placebo. There were 13 infants who received one or more doses but did not complete the study, including 10 in the vaccine group, and 3 in the placebo group. Withdrawal from the study was because of relocation out of the area or reluctance to make study follow-up visits. No infants were withdrawn because of adverse events. These infants are included in the analysis of reactions for doses that they received, but only the 312 infants who were followed during the subsequent rotavirus season are considered in the analysis of protective efficacy.

Vaccination took place primarily during the summer and fall. The first dose of vaccine was administered on Jun. 18, 1992, and the last booster dose was administered on Feb. 11, 1992. 257 subjects (79%) had received all 3 doses Jan. 1, 1993. Demographic features of the study population were similar in both vaccine and placebo groups, as shown in Table 3 below.

TABLE 3

Characteristics of the Study Population

|  | Vaccine (n = 207) | Placebo (n = 118) |
| --- | --- | --- |
| Mean age at enrollment (days) | 126.0 | 121.4 |
| Age range (days) | 53–261 | 57–271 |
| No. breast feeding (%) | 74 (35.7) | 55 (46.6) |
| No. with sibs ≦3 y.o. (%) | 72 (34.8) | 36 (30.5) |
| No. in day care (%) | 27 (13.0) | 16 (13.6) |

A. Vaccine

The vaccine consisted of $10^{7.3}$ plaque forming units per dose of WI79-3,9 virus administered by mouth in a total volume of 2.5 ml containing 0.25 ml WI79-3,9 virus suspension, 1.75 ml sterile Eagle's minimal essential media (MEM), and 0.5 ml cherry syrup (Philadelphia Extract Co.). The WI79-3,9 virus was prepared as described in Example 2B above. Placebo consisted of 2 ml of MEM and 0.5 ml cherry syrup. Vaccine and placebo were supplied as individual doses which were stored at minus 20° C. and thawed immediately prior to use.

B. Laboratory Studies

Diarrheal stools were tested for the presence of rotavirus by enzyme immunoassay. Samples collected in Rochester were tested using the Pathfinder (Kallestadt Diagnostics, Austin, Tex.), while those collected in Philadelphia were tested using the Rotaclone (Cambridge Biosciences, Boston, Mass.) EIA kits. All positive samples were confirmed by polyacrylamide gel electrophoresis [K. Dolan et al, *J. Clin. Microbiol.*, 21:753–758 (1985)]. The serotype of the rotaviruses detected in the study was determined by polymerase chain reaction as previously described [J. Gentsch et al, cited above and V. Gouvea et al, *J. Clin. Microbiol.*, 28:276–282 (1990)].

C. Clinical Studies

Infants in the study were healthy, between the ages of 2 and 8 months at the time of the first vaccination, and had received at least one previous dose of oral polio and DPT vaccine. Infants were excluded from participation if they had significant chronic illness. Vaccination was postponed if symptoms of acute gastrointestinal illness or fever were noted. The number and ages of household contacts, attendance at day care, and breast feeding history were recorded at enrollment.

Infants were assigned to receive vaccine or placebo in double-blind fashion using a block randomization scheme. Three doses of vaccine or placebo were administered, separated by approximately 2 month intervals. Subjects were not fed for one hour before each vaccination, and breast feeding was withheld for 1 hour afterwards as well. Subjects enrolled in Rochester received 30 ml of soy-based infant formula containing 400 mg sodium bicarbonate, followed by 2.5 ml of vaccine or placebo. At the Philadelphia site, subjects were given 2.5 ml of vaccine or placebo after ingesting at least 30 mls of either soy or milk-based infant formula. No sodium bicarbonate was added to the formula of the Philadelphia subjects. The interval between study vaccination and receipt of other routine vaccinations was at least 7 days.

Each family was given symptom cards, a thermometer, and an instruction sheet and materials for stool specimen collection after each vaccination. Parents were requested to keep a record of the number and consistency of each stool passed by subjects in the first 7 days after each vaccination, and to measure the rectal temperature of the infant daily between 4 and 8 pm. In addition, a member of the study team called the parents once between days 3 and 5 following vaccination for direct ascertainment of reactogenicity.

Participants were monitored throughout the following winter and spring to determine the incidence of rotavirus gastroenteritis. Surveillance commenced on Jan. 1, 1993 with the first reported case of rotavirus in ongoing community surveillance programs, and continued until Jun. 15, 1993 which was 2 weeks after the last case of rotavirus gastroenteritis in the surveillance program at either site. Participating families were contacted by telephone on a weekly basis during this period to inquire about symptoms of gastroenteritis. Parents collected at least one stool specimen from the subject, and recorded daily temperatures and other information during gastrointestinal illness, including the presence of irritability, the number of episodes of vomiting, and the number and consistency of stools.

The following definitions were used in the study: gastroenteritis was defined as the presence of one watery stool or three or more liquid stools and/or one or more episodes of vomiting in a 24 hour period; rotavirus gastroenteritis was defined as the presence of gastroenteritis with identification of rotavirus in at least one stool specimen; and clinically significant rotavirus gastroenteritis was defined as rotavirus gastroenteritis with a clinical symptom score of >8, using a scoring system previously utilized in evaluating the efficacy of the WC3 virus [H. F. Clark et al, cited above]. Gastroenteritis episodes were scored according to the information provided by the parents during the surveillance period. All diagnoses and gastroenteritis scores were confirmed by at least 2 members of the study team prior to unblinding of the study.

D. Results

The statistical significance of differences in rates between vaccine and placebo groups was calculated using corrected chi-square tests or Fisher's exact test as appropriate. Confidence limits for protective efficacy were calculated as described by D. Kleinbaum et al, *Lifetime Learning Publications* (1982).

1. Reactions Following Vaccination

The WI79-3.9 virus was well tolerated at a dose of $10^{7.3}$ PFU in young infants. Rates of reactions were generally similar in infants enrolled in Rochester and Philadelphia, and the data have been combined for presentation in Table 4 below.

2. Protection From Rotavirus Gastroenteritis

The epidemic curves of the outbreaks of rotavirus gastroenteritis in Rochester and Philadelphia were typical of rotavirus in these geographic areas. The first case of laboratory documented rotavirus gastroenteritis was noted in week 2 of 1993 in Rochester and in week 5 of Philadelphia. Although some subjects experienced more than one episode of gastroenteritis during the surveillance period, no subject experienced more than one episode of rotavirus gastroenteritis at either study site.

The distribution of episodes of gastroenteritis in vaccine and placebo recipients at both sites during the surveillance period is shown in Table 5 below. In this table, the subjects

TABLE 4

Rates of Reactions within 7 days of Administration of WI79-3,9 Virus Vaccine

| Group | Dose | No. (%) Returning Records | Temp ≥ 38.0° C. | vomiting | diarrhea | Altered behavior |
|---|---|---|---|---|---|---|
| Vaccine | Dose 1 | 193(93.2) | 16(8.3) | 29(15.0) | 29(15.0) | 60(31.1) |
| (n = 207) | Dose 2 | 183(88.4) | 22(12.0) | 18(9.8) | 51(27.9) | 45(24.6) |
|  | Dose 3 | 175(84.5) | 37(21.1) | 18(10.3) | 41(23.4) | 42(24.0) |
| Placebo | Dose 1 | 113(95.8) | 16(14.1) | 26(23.0) | 31(27.4) | 40(35.4) |
|  | Dose 2 | 103(87.3) | 17(16.3) | 21(20.4) | 28(27.2) | 31(30.1) |
|  | Dose 3 | 95(80.5) | 18(18.9) | 11(11.6) | 26(27.3) | 29(30.5) |

\*= Reported as percent of those returning records

There were no reactions that occurred at significantly higher frequency in vaccine than in placebo recipients. In particular, the rate of fever following vaccination was low, and was similar in vaccine and placebo recipients. When fever occurred it was generally low grade. Rectal temperatures of $\geq 38.6°$ C. following dose 1, 2, or 3 were seen in 2.1, 2.7, and 6.2% of vaccine recipients, and in 4.4, 2.9, and 4.2% of placebo recipients respectively. There was also no evidence of clustering of days of fever in vaccine recipients, as approximately equal proportions of subjects in each group were febrile on each of the seven days following vaccination.

were followed during the rotavirus season. For purposes of this study, rotavirus gastroenteritis was defined as occurrence of vomiting and/or of one watery stool or three or more loose stools in association with detection of rotavirus in an acute stool specimen.

TABLE 5

Protective Efficacy of the WI79-3,9 Vaccine Virus Against all Rotavirus (RV) Gastroenteritis and Clinically Significant RV Gastroenteritis in the Surveillance Period

| Site | Group | No. of Subjects | No. of Subjects (%) with RV gastroenteritis | % Protection Against RV Gastroenteritis (95% CI) | No. Subjects (%) with Clinically Significant RV Gastroenteritis | % Protection Vs. Clinically Significant Gastroenteritis (95% CI) |
|---|---|---|---|---|---|---|
| Rochester | placebo | 74 | 19 (25.7) |  | 12 (16.2) |  |
|  |  |  |  | 64.1 (32.5,80.9)‡ |  | 83.7 (51.4,94.6)§ |
|  | vaccine | 152 | 14 (9.2) |  | 4 (2.6) |  |
| Philadelphia | placebo | 41 | 7 (17.1) |  | 6 (14.6) |  |
|  |  |  |  | 74.0 (−18.2,94.3)l |  | 100¶ |
|  | vaccine | 45 | 2 (4.5) |  | 0 (0.0) |  |
| Total | placebo | 115 | 26 (22.6) |  | 18 (15.7) |  |
|  |  |  |  | 64.1 (35.9,79.9)\*\* |  | 87.0 (62.6,95.5)†† |
|  | vaccine | 197 | 16 (8.1) |  | 4 (2.0) |  |

‡- P = 0.001, §- P = 0.0001, l- P = 0.078, ¶- confidence limits not calculated, P = 0.009, \*\*- P = 0.0004, ††- P = 0.000008.

The WI79-3.9 virus vaccine was highly effective in the prevention of clinically significant rotavirus gastroenteritis, as defined by a severity score of >8. The differences between vaccine and placebo recipients in the proportions of subjects experiencing clinically significant rotavirus gastroenteritis were statistically significant at both study sites, with an 84% reduction in Rochester (P=0.0001) and a 100% reduction in Philadelphia (P=0.009). When the results at the two study sites were combined, the vaccine protective efficacy against clinically significant rotavirus gastroenteritis was 87.0%. Clinically significant rotavirus disease occurred in only 4 of 195 (2.1%) infants receiving vaccine. Vaccines was also associated with a 64.1% reduction in all rotavirus episodes in Rochester (P=0.001) and a 74.0% reduction in Philadelphia (P=NS).

As noted previously, 21% of the subjects did not receive all three dose of vaccine before the beginning of the circulation of wild-type rotavirus in the community. Therefore, asymptomatic wild-type infections could have contributed to the protective efficacy seen in the study. However, the protective efficacy of the WI79-3,9 vaccine was similar when only those children who completed all three doses of vaccine before January 1 were considered. Rotavirus gastroenteritis was seen among children who completed all three doses before this date in 20 of 96 placebo recipients and 15 of 161 vaccine recipients (55.3% protective efficacy, P=0.009), and clinically significant rotavirus gastroenteritis was seen in 14/96 such placebo recipients and 3/161 such vaccine recipients (87.2% protective efficacy, P=0.00007).

Since rotavirus is known to cause a relatively severe dehydrating gastroenteritis, it was also of interest to determine the overall effect of vaccination with WI79-3,9 vaccine on gastroenteritis-related morbidity in the study population. There were no hospitalizations or emergency room visits for gastroenteritis in the study participants. However, subjects who received the WI79-3,9 vaccine had lower rates of several measurements of gastroenteritis morbidity (Table 6).

TABLE 6

Impact of Winter Gastroenteritis in the Study Population

| Event | No. (No. per subject) in those receiving: | | Percent Reduction in Vaccine Recipients |
|---|---|---|---|
| | Placebo (115 subjects) | Vaccine (197 subjects) | |
| Episodes of any gastroenteritis | 79 (0.69) | 81 (0.41) | 40.1% |
| Episodes of clinically significant gastroenteritis | 34 (0.30) | 20 (0.10) | 65.7% |
| Days of gastrointestinal illness | 377 (3.28) | 311 (1.58) | 51.8% |
| MD visits | 26 (0.23) | 23 (0.12) | 48.4% |
| Episodes requiring ORT | 24 (0.21) | 25 (0.13) | 39.2% |

Overall, the risk of experiencing any clinically significant gastroenteritis was reduced 64.9% by vaccination. In addition, the average number of days of gastroenteritis per child during the observation period was reduced by 50.6% in the vaccine recipients. Vaccine recipients experienced 317 fewer days of diarrhea than expected based on the rate in the placebo group, and required 20 fewer than expected pediatrician visits for gastroenteritis. Other measures of gastroenteritis morbidity, including use of oral rehydration, antipyretics, and episodes treated empirically with antimicrobial therapy were similarly reduced in vaccine recipients.

3. Serotype of Natural Rotavirus Challenge

Serotype G1 clearly predominated in each community. All of the rotaviruses detected in the Philadelphia area were serotype G1 by PCR typing. Of the 19 symptomatic rotavirus infections in placebo recipients in Rochester, 15 were G1, 1 was G4, and 3 samples did not have sufficient material for typing. Of the 14 symptomatic infections in vaccine recipients, 11 were type G1, 1 was type G3, and 2 were unable to be typed. PCR analysis for human P type was also performed on 16 samples from Rochester (7 from vaccine and 9 from placebo recipients), and all were P type 1.

E. Conclusions

This study demonstrates that the WI79-3,9 rotavirus, a reassortant between the bovine rotavirus WC3 and the human serotype G1 rotavirus WI79, is well tolerated when given as a three dose regimen in infants, and is highly effective at prevention of clinically significant serotype G1 human rotavirus infection. Infants immunized with the WI79-3,9 virus had lower rates of rotavirus gastroenteritis, less diarrhea, and required less pediatric care than did placebo recipients. Confidence limits (CI) for efficacy were calculated as described by Kleinbaum et al, *Epidemiologic Research: Principles and Quantitative Methods*, Lifetime Learning Publications (1982). The protective efficacy of the WI79-3,9 vaccine was 87.0% (95% CI 62.6–95.5%) against clinically significant rotavirus gastroenteritis (rotavirus gastroenteritis with a clinical severity score of >8), and was 64.1% (95% CI 35.9–79.9%) against all rotavirus episodes. This level of protective efficacy of the WI79-3,9 virus is similar to that previously reported for two doses of the WI79-3,9 virus in small field trials conducted in Philadelphia [H. F. Clark et al, cited above] and Rochester [C. Christy et al, cited above] during predominantly serotype 1 rotavirus seasons. Thus, the WI79-3,9 virus has several desirable qualities as a live vaccine, i.e., it is highly attenuated in the target population, and induces effective protective immunity. Since the virus appears to be shed at extremely low levels in the stools of infected individuals, it is also unlikely to be transmitted efficiently to susceptible contacts, and unlikely to undergo genetic reversion during replication in vaccinees, although these characteristics have not been studied extensively.

In this trial, post season sera were not obtained, so the rate of rotavirus infection was not evaluated serologically. It is unlikely however, that the WI79-3,9 vaccine prevented asymptomatic rotavirus infection, based on the results of previous trials of the WI79-3,9 virus [H. F. Clark et al, cited above] and other live, attenuated rotavirus vaccines [H. F. Clark et al, cited above and H. Madore et al, *J. Infect. Dis.*, 166:235–243 (1992)].

EXAMPLE 6

Immunogenicity of Heterologous v.p.4/v.p.7 Rotavirus Reassortant Vaccine

The following study illustrates that a WC3/human reassortant composition containing human v.p.4 and human v.p.7 on separate reassortants elicits a stronger immune response than a composition containing human v.p.4 and human v.p.7 in a single reassortant.

In infants, a clinical trial was conducted in which the administration of the WI79-4,9 vaccine, containing a reassortant having both human v.p. 4 and human v.p. 7 antigens therein, was compared with administration of an equal-titered vaccine mixture of WI79-4 (human v.p. 4 and bovine v.p. 7 antigens) and the human type 1 v.p.7 reassortant WI79-3,9 (bovine v.p. 4 and human v.p. 7 antigens).

The infants, who were between 2 and 11 months of age, were first tested for the presence of rotavirus neutralizing antibody in a conventional serum virus neutralization antibody assay. For these tests, blood was withdrawn, the serum separated, and the assay was performed using each parent rotavirus, e.g., WC3 and WI79. Infants were scored either originally sero-negative or originally sero-positive.

Then a group of infants was administered orally a 2.5 ml dose of the WI79-4 and WI79-3,9 vaccine mixture or the WI79-4,9 vaccine. Thirty days later, the infants were administered orally a second 2.5 ml dose of the same vaccine they received before. At the administration of the second dose and again 30 days after the second dose of vaccine, the infants were tested for the presence of rotavirus neutralizing antibody in the same assay.

According to this trial, a positive immune response to either parental virus (WC3 or WI79) in the serum virus neutralization assay was defined as the development of a serum virus neutralization titer greater than 1:125 in an originally sero-negative infant. In the case of an originally sero-positive infant, an increase in the titer of three-fold or more was considered a positive immune response.

The results obtained are reported in terms of virus neutralizing antibody. Results reveal that two doses of mixed WI79-4 and WI79-3,9 vaccine induced neutralizing antibody to WC3 in 27/27 infants and to type 1 WI79 rotavirus in 21/27 (78%). Two doses of the reassortant WI79-4,9 vaccine induced antibody to type 1 WI79 rotavirus in 9/26 infants (35%) and to WC3 in 7/27 infants (26%).

These results illustrate that the mixture of reassortants each having heterologous species as well as human type rotavirus surface antigens (i.e., human and bovine v.p.4 and v.p.7 containing reassortants) is more immunogenic in infants than a reassortant bearing exclusively human type virus surface antigens (i.e., human v.p.4 and human v.p. 7).

EXAMPLE 7

Quadrivalent Reassortant Vaccine

The quadrivalent vaccine contained WI79-3,9 (G1), WISC2-4,9 (G2), WI78-8 (G3), and WI79-4 (P1). Vaccine formulation was essentially as described for the WI79-3,9 trial in Example 5. Preliminary analysis of this trial is as follows.

Briefly, vaccine protocol was a pilot, double-blind, placebo-controlled, multicenter trial to evaluate the efficacy in healthy infants of a 3 dose regimen. Each infant was enrolled to receive the first dose at 2–6 months of age, with the second and third doses approximately 2 and 4 months after dose 1. For evaluation of efficacy, a case of rotavirus disease in study participants had to meet both of the following criteria: (1) three or more watery or looser than normal stools with a 24 hour period and/or forceful vomiting. (2) Rotavirus identified by ELISA in a stool specimen taken within 7 days of the onset of symptoms. Electropherotype analysis for virus genomic RNA was employed in order to confirm the presence of rotavirus in fecal specimens. For final analysis, 199 evaluable subjects received vaccine and 206 received placebo.

Based on ELISA positive cases, the rotavirus vaccine was 67.1% efficacious (95% C1 of [39.9%, 81.9%]) in preventing all disease and 68.6% efficacious (95% Cl of [36.4, 84.5%]) in preventing clinically significant disease. Statistical analysis revealed that the proportion of rotavirus cases in the vaccine group (14/199) was significantly lower ($p<0.001$) than the proportion of rotavirus cases in the placebo group (44/206). The proportion of clinically significant cases in the vaccine group (10/199) was also significantly lower than the proportion of clinically significant cases in the placebo group (33/206).

Based on ELISA and electropherotype positive cases, the rotavirus vaccine was 72.9% efficacious (95% Cl of [47.3%, 86.0%]) in preventing all disease, and 72.6% efficacious (95% Cl of [42.9%, 86.9%]) in preventing clinically significant disease. Statistical analysis revealed that the proportion of rotavirus cases in the vaccine group (11/199) was significantly lower ($p<0.001$) than the proportion of rotavirus cases in the placebo group (42/206). The proportion of clinically significant cases in the vaccine group (9/199) was also significantly lower than the proportion of clinically significant cases in the placebo group (34/206).

Severity scores ≧16 were noted in 11/42 of placebo recipients (26%) while only one vaccine recipient had a severity score of 16, and no vaccine recipient had a score >16, indicating that the vaccine was highly effective in preventing the most severe cases of rotavirus disease.

In order to detect vaccine shedding, 854 of 859 available fecal specimens have been cultured. No shedding was detected in placebo recipients. Rotavirus shedding was observed in 13 specimens from 12 vaccine recipients. Nine of these episodes occurred 3–5 days after the first vaccine dose and two participants shed rotavirus at day 7–9 after dose one. Electropherotype analysis of plaque-purified rotavirus indicated that the 12 vaccine recipients each shed P1 vaccine strain. In 5 of these 12 cases, a second rotavirus was detected, which appears to be serotype P1G1. The P1G1 serotype was most likely generated in vivo rather than during subsequent tissue culture passage.

Numerous modifications may be made by one skilled in the art to the methods and compositions of the present invention in view of the disclosure herein. Such modifications are believed to be encompassed in the appended claims.

What is claimed is:

1. Rotavirus reassortant of G1 serotype, WI79-3,9.

2. Rotavirus reassortant of G3 serotype, WI78-8.

3. Rotavirus reassortant of G2 serotype, WI79-3+WISC2-9.

4. Rotavirus reassortant of G4 serotype, Bricout B-9.

5. A vaccine useful in reducing the clinical symptoms associated with gastroenteritis caused by rotavirus infection comprising rotavirus reassortant WI79-3,9.

6. The vaccine according to claim 5 further comprising at least one additional rotavirus reassortant selected from the group consisting of WI78-8, WI79-3+WISC2-9, and Bricout B-9.

7. The vaccine according to claim 6 comprising rotavirus reassortants WI79-3,9, WI78-8, WI79-3+WISC2-9, and Bricout B-9.

8. The vaccine according to claim 6 comprising rotavirus reassortants WI79-3,9, WI79-3+WISC2-9, and WI78-8.

9. The vaccine according to claim 5 wherein said vaccine contains additional immunizing antigens.

10. The vaccine according to claim 9 wherein said vaccine further contains polio antigens.

11. A rotavirus reassortant having RNA comprising a gene segment encoding viral protein (v.p.) 4 derived from a human rotavirus strain and ten gene segments derived from a human rotavirus strain and the bovine strain WC3 or progeny thereof, said reassortant suitable for use in a human vaccines, wherein at least one of said ten gene segments is derived from the bovine strain.

12. The reassortant according to claim 11, wherein the human strain is selected from the group consisting of WI78, WI79, WISC2, WI61, Bricout B, and DS1.

13. The reassortant according to claim 11, wherein the reassortant consists of a gene segment encoding v.p. 4 antigen derived from a human rotavirus strain and the remaining ten gene segments derived from the bovine WC3 rotavirus strain.

14. The reassortant according to claim 13, wherein said reassortant is selected from the group consisting of WI79-4; WI78-4; DS1-4; Bricout B-4; WISC2-4; and WI61-4.

15. A vaccine useful in reducing the clinical symptoms associated with gastroenteritis caused by rotavirus infection comprising:
   (a) a first rotavirus reassortant having RNA comprising a gene segment encoding vital protein (v.p.) 4 derived from a selected human rotavirus strain and ten gene segments derived from a human rotavirus strain and bovine rotavirus strain WC3 or progeny thereof, wherein at least one of said ten gene segments is derived from the bovine rotavirus strain; and
   (b) a second rotavirus reassortant having RNA comprising a gene segment encoding viral protein (v.p.) 7 derived from a selected human rotavirus strain, and ten gene segments derived from a human rotavirus strain and bovine rotavirus strain WC3 or progeny thereof, wherein at least one of said ten gene segments is derived from the bovine strain;
   wherein said reassortants are suitable for use in a human vaccine.

16. The vaccine according to claim 15, comprising rotavirus reassortants WI79-4, WI79-3,9, WI78-8, Bricout B-9 and WI79-3+WISC2-9.

17. The vaccine according to claim 15 comprising rotavirus reassortants WI79-4 and WI79-3,9.

18. The vaccine according to claim 15 comprising rotavirus reassortants WI79-4, WI79-3,9, WI79-3+WISC2-9, and WI78-8.

19. The vaccine according to claim 15, comprising rotavirus reassortants WI79-4, DS1-4, WI79-3,9, WI78-8, Bricout B-9 and WI79-3+WISC2-9.

20. Rotavirus reassortant WI79-4,9, deposited as American Type Culture Collection accession number VR2415.

21. Rotavirus reassortant WI78-1,6-11, deposited as American Type Culture Collection accession number VR2195.

22. A vaccine useful in reducing the clinical symptoms associated with gastroenteritis caused by rotavirus infection comprising a rotavirus reassortant selected from the group consisting of WI78-8, WI79-3+WISC2-9, and Bricout B-9.

23. A vaccine useful in reducing the clinical symptoms associated with gastroenteritis caused by rotavirus infection comprising:
   a rotavirus reassortant having RNA comprising a gene segment encoding vital protein (v.p.) 4 derived from a human rotavirus strain and ten gene segments derived from a human rotavirus strain and the bovine rotavirus strain WC3 or progeny thereof, said reassortant useful in a human vaccine, wherein at least one of said ten gene segments is derived from the bovine strain.

24. The vaccine according to claim 23 wherein the rotavirus reassortant is selected from the group consisting of WI79-4, WI78-4, DS1-4, and WI61-4.

25. The vaccine according to claim 24 wherein the vaccine comprises WI79-4 reassortant deposited as American Type Culture Collection accession number VR2377.

26. The reassortant according to claim 1 selected from the group consisting of the reassortant passages deposited as American Type Culture Collection accession numbers VR2194 and VR2196.

27. The reassortant according to claim 2 consisting of the reassortant deposited as American Type Culture Collection accession number VR2494.

28. The reassortant according to claim 3 consisting of the reassortant deposited as American Type Culture Collection accession number VR2493.

29. The reassortant according to claim 4 consisting of the reassortant deposited as American Type Culture Collection accession number VR2492.

30. The vaccine according to claim 5 wherein the WI79-3,9 reassortant is selected from the group consisting of the reassortant passages deposited as American Type Culture Collection accession numbers VR2194 and VR2196.

31. The vaccine according to claim 6 wherein the WI78-8 reassortant is deposited as American Type Culture Collection (ATCC) accession number VR2494, the WI79-3+WISC2-9 reassortant is deposited as ATCC accession number VR2493, and the Bricout B-9 reassortant is deposited as ATCC accession number VR2492.

32. The vaccine according to claim 14 wherein the WI79-4 reassortant is deposited as American Type Culture collection accession number VR2377.

33. The vaccine according to claim 16 wherein the WI79-4 reassortant is deposited as American Type Culture Collection (ATCC) accession number VR2377, the WI79-3,9 reassortant is selected from the group consisting of reassortant passages deposited as ATCC accession number VR2194 and VR2196, the WI78-8 reassortant is deposited as ATCC accession number VR2494, the Bricout B-9 reassortant is deposited as ATCC accession number VR2492, and the WI79-3+WISC2-9 reassortant is deposited as ATCC accession number VR2493.

34. The vaccine according to claim 17 wherein the WI79-4 reassortant is deposited as American Type Culture Collection (ATCC) accession number VR2377 and the WI79-3,9 reassortant is selected from the group consisting of the passages deposited as ATCC accession number VR2194 and VR2196.

35. The vaccine according to claim 18 wherein the WI79-4 reassortant is deposited as American Type Culture Collection (ATCC) accession number VR2377, the WI79-3,9 reassortant is selected from the group consisting of the passages deposited as ATCC accession number VR2194 and VR2196, the WI79-3+WISC2-9 reassortant is deposited as ATCC accession number VR2493, and the WI78-8 reassortant is deposited as ATCC accession number VR2494.

36. The vaccine according to claim 19 wherein the WI79-4 reassortant is deposited as American Type Culture collection (ATCC) accession number VR2377, the WI79-3,9 reassortant is selected from the group consisting of the passages deposited as ATCC accession number VR2194 and VR2196, the WI78-8 reassortant is deposited as ATCC accession number VR2494, the Bricout B-9 reassortant is deposited as ATCC VR2492, and the WI79-3+WISC2-9 reassortant is deposited as ATCC accession number VR2493.

37. A method of vaccinating a human infant or child against severe rotavirus infection or preventing such infection comprising administering to said infant or child a vaccine according to any one of claims 5–10, 15–19, 22–25, and 30–36.

38. The method according to claim 37 wherein said vaccine is administered orally.

39. The vaccine according to any one of claims 5–10, 15–19, 22–25, or 30–36, further comprising an adjuvant.

* * * * *

UNITED STATES PATENT AND TRADEMARK OFFICE
CERTIFICATE OF CORRECTION

PATENT NO. : 5,626,851
DATED : May 6, 1997
INVENTOR(S) : H Fred Clark, Paul Offit, and Stanley A. Plotkin It is certified that error appears in the above-indentified patent and that said Letters Patent is hereby corrected as shown below:

Col. 4, line 27, delete "WCS," and insert in place thereof -- WC8, --.

Col. 20, Claim 11, line 58, delete "vaccines," and insert in place thereof -- vaccine, --.

Col. 21, Claim 15, line 8, delete "vital" and insert in place thereof -- viral --.

Col. 21, Claim 23, line 47, delete "vital" and insert in place thereof -- viral --.

Signed and Sealed this

Seventh Day of October, 1997

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

| | |
|---|---|
| PATENT NO. | : 5,626,851 |
| APPLICATION NO. | : 08/353547 |
| DATED | : May 6, 1997 |
| INVENTOR(S) | : H. Fred Clark, Paul Offit and Stanley A. Plotkin |

It is certified that error appears in the above-identified patent and that said Letters Patent is hereby corrected as shown below:

Title Page;
On the face of the patent, the Related U.S. Application Data in paragraph 63 reading "Sep. 14, 1990" should read --Sep. 14, 1993--.

On the face of the patent, the Related U.S. Application Data in paragraph 63 reading "Jul. 2, 1990" should read --Jul. 26, 1990--.

Column 1, line 7, reading "Sep. 14, 1990" should read --Sep. 14, 1993--.

Signed and Sealed this

Eighteenth Day of December, 2007

JON W. DUDAS
*Director of the United States Patent and Trademark Office*